(12) United States Patent
Kim

(10) Patent No.: US 6,915,161 B2
(45) Date of Patent: *Jul. 5, 2005

(54) METHOD AND DEVICE FOR SENSING ATRIAL DEPOLARIZATIONS DURING VENTRICULAR TACHYCARDIA

(75) Inventor: Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/700,373

(22) Filed: Nov. 3, 2003

(65) Prior Publication Data

US 2004/0176808 A1 Sep. 9, 2004

Related U.S. Application Data

(63) Continuation of application No. 09/822,784, filed on Mar. 30, 2001, now Pat. No. 6,643,547.

(51) Int. Cl.[7] ................................................. A61N 1/18
(52) U.S. Cl. .......................................... 607/14; 607/17
(58) Field of Search .............................. 607/4, 5, 9, 11, 607/14, 17, 27, 28, 46

(56) References Cited

U.S. PATENT DOCUMENTS

| | | | |
|---|---|---|---|
| 4,825,870 A | 5/1989 | Mann et al. | 128/419 PG |
| 4,974,589 A | 12/1990 | Sholder | 128/419 PG |
| 5,103,820 A | 4/1992 | Markowitz | 128/419 OPG |
| 5,129,393 A | 7/1992 | Brumwell | 128/419 PG |
| 5,144,949 A | 9/1992 | Olson | 128/419 PG |
| 5,273,035 A | 12/1993 | Markowitz et al. | 607/14 |
| 5,312,445 A * | 5/1994 | Nappholz et al. | 607/9 |
| 5,342,405 A | 8/1994 | Duncan | 607/17 |
| 5,400,796 A | 3/1995 | Wecke | 128/705 |
| 5,534,016 A * | 7/1996 | Boute | 607/9 |
| 5,591,214 A | 1/1997 | Lu | 607/9 |
| 5,658,320 A | 8/1997 | Betzold et al. | 607/14 |
| 5,776,167 A | 7/1998 | Levine et al. | 607/9 |
| 5,893,882 A | 4/1999 | Peterson et al. | 607/14 |
| 6,091,988 A | 7/2000 | Warman et al. | 607/5 |
| 6,459,932 B1 | 10/2002 | Mehra | 607/5 |
| 6,477,420 B1 | 11/2002 | Struble et al. | 607/14 |
| 6,643,547 B2 * | 11/2003 | Kim | 607/14 |

* cited by examiner

Primary Examiner—Tu Hoang
(74) Attorney, Agent, or Firm—Schwegman, Lundberg, Woessner & Kluth, P.A.

(57) ABSTRACT

A cardiac rhythm management device is disclosed which incorporates an improved method for sensing atrial depolarizations during episodes of ventricular tachycardia. The atrial sensing channel is blanked for a specified blanking interval after detection of a ventricular sense. When the ventricular rate is above a specified limit rate, the blanking interval for the atrial sensing channel is either shortened or blanking is discontinued altogether in order to allow sensing of atrial depolarizations that occur shortly after a ventricular sense.

17 Claims, 3 Drawing Sheets

METHOD AND DEVICE FOR SENSING ATRIAL DEPOLARIZATIONS DURING VENTRICULAR TACHYCARDIA

CROSS-REFERENCE TO RELATED APPLICATION(S)

This application is a continuation of U.S. patent application Ser. No. 09/822,784, filed on Mar. 30, 2001, now U.S. Pat. No. 6,643,547, the specification of which is incorporated herein by reference.

FIELD OF THE INVENTION

This invention pertains to cardiac rhythm management devices and methods. In particular, the invention relates to methods for the detection of atrial and ventricular tachyarrhythmias.

BACKGROUND

Tachyarrhythmias are abnormal heart rhythms characterized by a rapid heart rate. Examples of tachyarrhythmias include supraventricular tachycardias such as atrial tachycardia and atrial fibrillation. The most dangerous tachyarrhythmias, however, are ventricular tachycardia and ventricular fibrillation. Ventricular rhythms occur when an excitatory focus in the ventricle usurps control of the heart rate from the sinoatrial node. The result is rapid and irregular contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus directly into the myocardium. Ventricular tachycardia is characterized by distorted QRS complexes occurring at a rapid rate, while ventricular fibrillation is diagnosed when the ventricle depolarizes in a chaotic fashion with no recognizable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachycardias. The electric shock terminates the tachycardia by depolarizing all excitable myocardium to render it refractory to further excitation. Implantable cardioverter/defibrillators (ICD's) provide this kind of therapy by delivering a shock pulse to the heart when fibrillation is detected by the device.

Another type of electrical therapy for tachycardia is antitachycardia pacing (ATP). In ATP, the heart is competitively paced with one or more pacing pulses in an effort to interrupt reentrant circuits causing the tachycardia. Modem ICD's have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in some patient discomfort owing to the high voltage of the shock pulses. It is desirable, therefore, for the ICD to use ATP to terminate a tachyarrhythmia whenever possible. Generally, only cardioversion/defibrillation will terminate fibrillation and certain high rate tachycardias, while ATP can be used to treat lower rate tachycardias. Cardioversion/defibrillation and anti-tachycardia pacing may also be used to treat atrial tachyarrhythmias, such as atrial fibrillation and atrial flutter. These tachyarrhythmias arise from excitatory foci in the atria. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium.

In current ICD's with ATP capability, ventricular fibrillation is distinguished from ventricular tachycardia using rate based criteria so that ATP or shock therapy can be delivered as appropriate. The heart rate is usually measured by detection of the time between successive R waves (i.e., ventricular depolarizations). A measured heart rate is classified as a tachycardia when the rate is in a ventricular tachycardia zone, defined as a range of rates above a specified tachycardia detection rate but below a specified fibrillation detection rate. A measured heart rate above the fibrillation detection rate is in the ventricular fibrillation zone and is classified as a fibrillation.

It is common in cardiac rhythm management devices with both atrial and ventricular sensing channels for the atrial sensing channel to be blanked after a ventricular sense for a specified blanking interval. This is done to avoid far-field sensing of ventricular depolarizations by the atrial sensing channel. If the ventricular rate is high, however, this may lead to undersensing of atrial depolarizations. Consequently, the atrial rate will be underestimated. This may lead to the device delivering ventricular anti-tachycardia therapy when a more appropriate therapy would be atrial anti-tachycardia therapy.

SUMMARY OF THE INVENTION

The present invention is a method and device for sensing atrial depolarizations during episodes of ventricular tachycardia. In most cardiac rhythm management devices that sense atrial and ventricular depolarizations, the atrial sensing channel is blanked for a specified blanking interval after detection of a ventricular sense. At high ventricular rates, atrial depolarizations may occur within the blanking interval and not be sensed. The atrial rate will then be underestimated, and an atrial tachyarrhythmia may go undetected. In accordance with the invention, when the ventricular rate is above a specified limit rate, the blanking interval for the atrial sensing channel is either shortened or blanking is discontinued altogether in order to allow sensing of atrial depolarizations that occur shortly after a ventricular sense. In the former case, the shortening of the blanking interval may be made to vary in accordance with the detected ventricular rate. In a further modification, the specificity of the atrial sensing channel may be increased when the blanking interval is shortened to lessen the possibility of far-field sensing. One way of doing this is to increase the sensing threshold of the atrial sensing channel.

The invention may be incorporated into a cardiac rhythm management device designed to treat atrial and ventricular arrhythmias by anti-tachycardia pacing and/or defibrillation shocks. In such a device, blanking of the atrial sensing channel may lead to delivery of ventricular anti-tachycardia pacing to inappropriately treat an atrial tachyarrhythmia. By correcting the underestimation of the atrial rate during such atrial tachyarrhythmias, the invention allows the device to deliver atrial anti-tachycardia pacing instead. In one embodiment, if a ventricular rate is detected which is above a specified limit rate but below a fibrillation detection rate, and the detected atrial rate is higher, a trial of atrial anti-tachycardia is delivered before delivery of either ventricular anti-tachycardia pacing or a ventricular defibrillation shock.

DETAILED DESCRIPTION

Currently available implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implantable cardiac rhythm management device. When a pacing pulse is delivered to a heart chamber, the resulting potential change appears at the input of the sensing channel for that chamber. In order to prevent saturation of the sense amplifier in this situation, the sensing channel can be blanked for a specified blanking interval by disabling the sense amplifier when a pace is delivered. During the blanking interval, the device thus ignores all electrical activity that appears at the input of the sensing channel. Blanking intervals can be used not only to shield the sensing channel from pacing artifacts, but can also be used to prevent crosstalk between sensing channels where depolarization occurring in one cardiac chamber is interpreted as a depolarization in another chamber. Such crosstalk occurs in the atrial sensing channel when a far-field sense resulting from a ventricular depolarization is interpreted as an atrial sense. Accordingly, a cross-chamber blanking interval for the atrial channel can be provided that is initiated after detection of a ventricular sense.

Because the cross-chamber blanking interval for the atrial sensing channel starts with a ventricular sense and lasts for a specified time thereafter, atrial depolarizations occurring shortly after ventricular depolarizations at high ventricular rates may fail to be detected. This may lead to the ventricular rate being erroneously measured as greater than the atrial rate in the case where the high ventricular rate is due to an atrial tachyarrhythmia. With an atrial tachyarrhythmia, the ventricles are actually being driven by impulses conducted from the rapidly beating atria. The ventricular rate can either be the same as the atrial rate if atrial excitation is conducted to the ventricles at a 1:1 ratio or can be less than the atrial rate if some degree of incomplete heart block is present such as during rapid atrial flutter or atrial fibrillation. With ventricular tachycardia, on the other hand, the ventricular rate is low enough that all of the ventricular impulses can be conducted retrogradely to the atria, and the atrial and ventricular rates are approximately the same. A cardiac rhythm management device that implements a cross-chamber blanking interval for the atrial sensing channel may thus fail to distinguish an atrial tachyarrhythmia from a ventricular tachycardia. Ventricular anti-tachycardia pacing may then be delivered by the device when atrial anti-tachycardia pacing or an atrial defibrillation shock is actually the appropriate therapy.

Figure 1A:
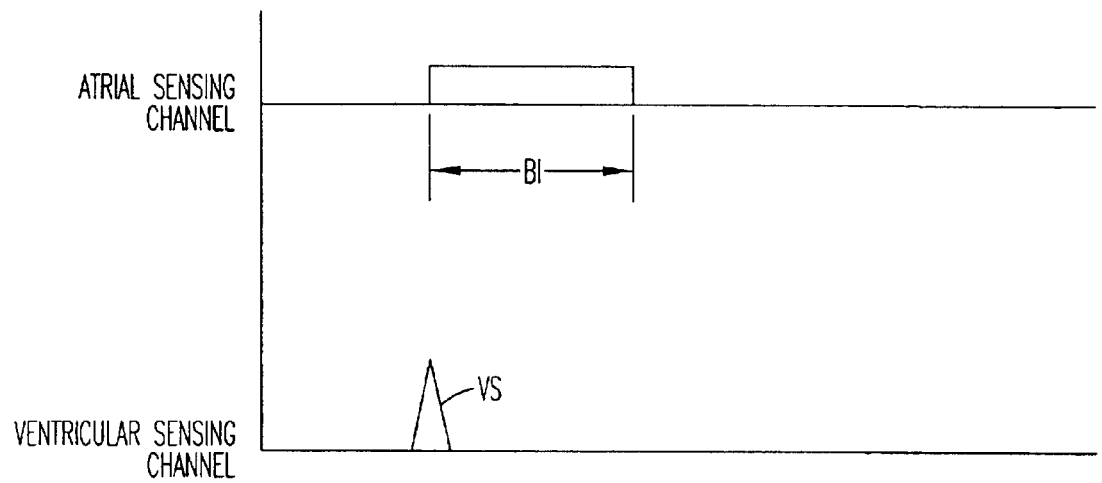
FIGS. 1A–B depict timelines for the atrial and ventricular sensing channels.
Figure 1B:
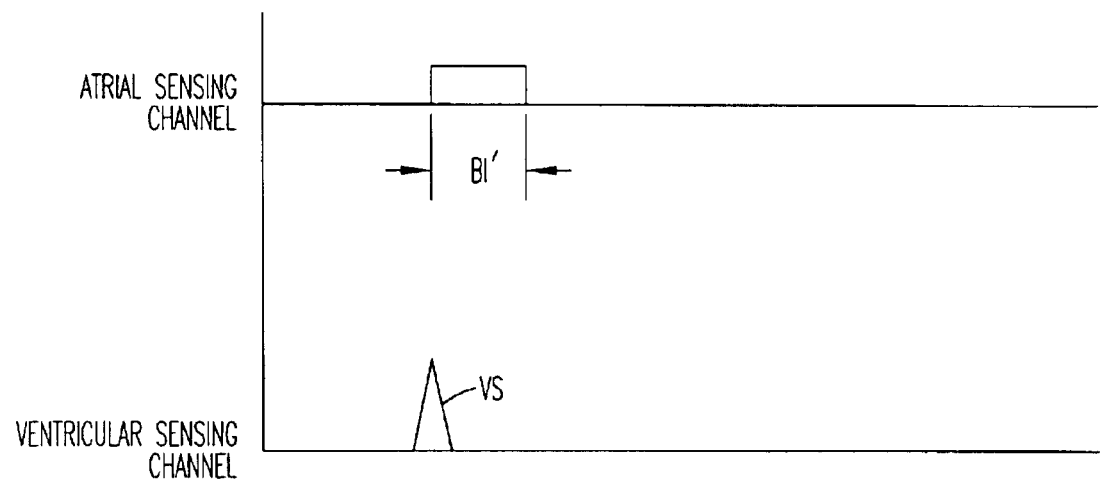

In accordance with the present invention, the atrial cross-chamber blanking interval is shortened when a ventricular rate above a specified limit rate is detected. In various embodiments, the blanking interval can be shortened by a predetermined amount, by an amount that varies with the ventricular rate, or reduced to zero to discontinue blanking. FIG. 1A is a timeline of the atrial and ventricular sensing channels showing the cross-chamber atrial sensing blanking interval BI being initiated by a ventricular sense VS in the ventricular sensing channel. FIG. 1B shows the situation when the ventricular rate has exceeded a specified limit rate, and a ventricular sense VS then initiates a shorter blanking interval BI'. The invention thus allows an atrial tachyarrhythmia to be correctly distinguished from a ventricular tachycardia, and the most appropriate therapy can be delivered.

For example, in one embodiment, a cardiac rhythm management device is configured so as to be capable of delivering anti-tachycardia pacing or defibrillation shocks to either the ventricles or the atria. Upon detection of a ventricular rate above the specified limit rate (but below the fibrillation detection rate, in which case a ventricular defibrillation shock would be delivered immediately), the blanking interval is shortened as described above. The device then compares the detected atrial rate with the detected ventricular rate. If the atrial rate is higher, atrial anti-tachycardia pacing (or an atrial defibrillation shock if the atrial rate is high enough) is delivered before ventricular anti-tachycardia pacing is tried.

Figure 2:
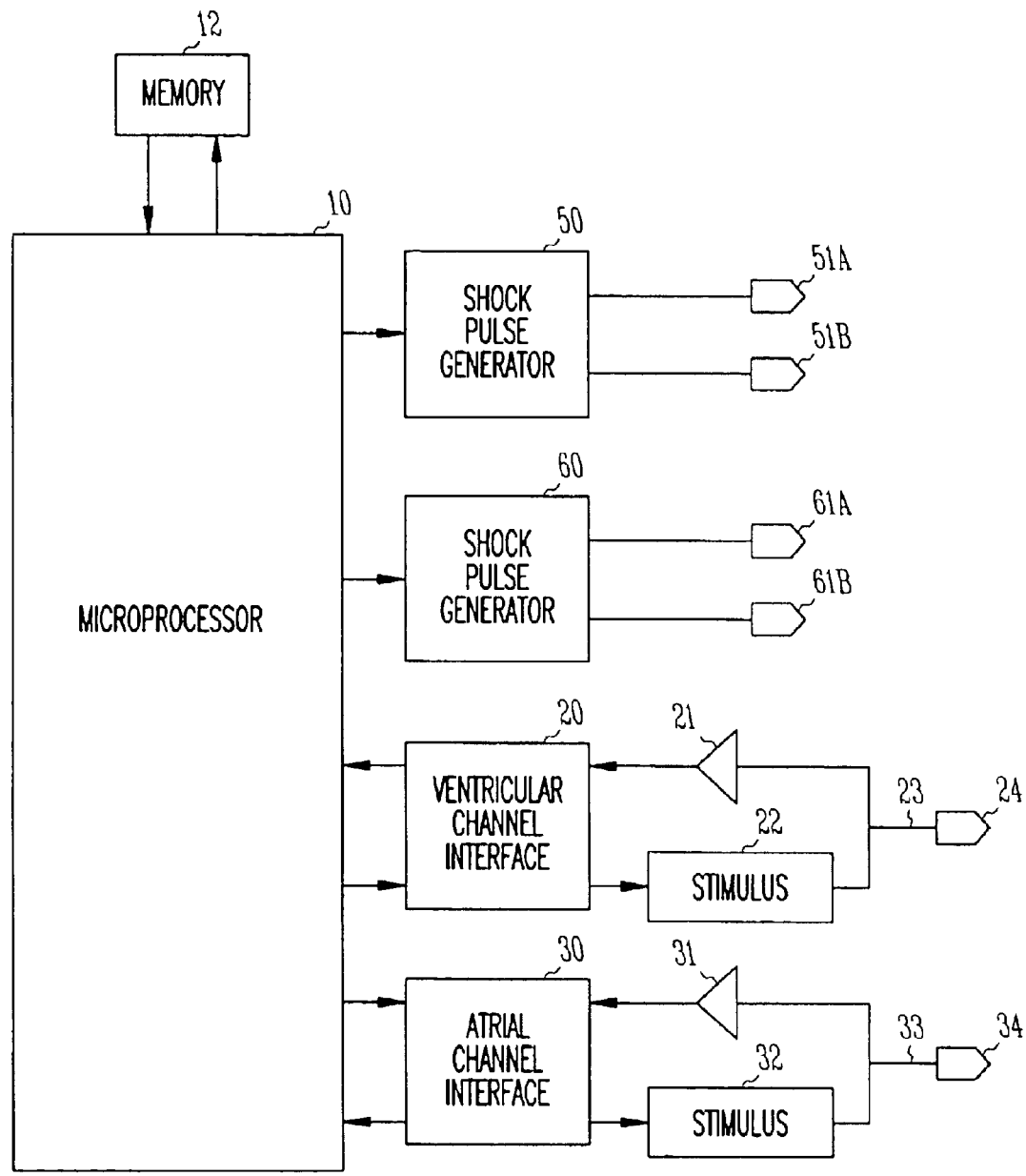
FIG. 2 is a block diagram of a cardiac rhythm management device.

FIG. 2 is a system diagram of a microprocessor-based implantable cardiac rhythm management device for treating atrial and ventricular tachyarrhythmias with either anti-tachycardia pacing or defibrillation shocks. The device may also incorporate a bradycardia pacing functionality. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The device has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The electrogram signals generated by the sensing amplifiers may either be fed to a comparator that inputs a digital signal to the controller or digitized by an analog-to-digital converter and then input to the controller. The gain of the amplifier in each sensing channel may be adjusted by the controller via an automatic gain control input AGC in accordance with sense signal amplitudes and/or measured noise levels. The sensing channels are used to control pacing and for measuring heart rate in order to detect tachyarrhythmias such as fibrillation. The device detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. A similar shock pulse generator 60 and shock electrodes 61a and 61b are provided to deliver ventricular fibrillation therapy.

In addition to blanking intervals, cardiac rhythm management devices also employ sensing refractory periods. A refractory period is an interval during which sensed activity from a sensing channel neither inhibits nor triggers a pacing pulse. Refractory periods are often implemented using a blanking interval such that the blanking interval constitutes the first part of the refractory period. Events can therefore be sensed by the hardware during the part of refractory period after the blanking interval ends but ignored by the software for purposes of triggering or inhibiting pacing pulses. Events sensed during the refractory period can, however, be used for other device algorithms such as those used to detect arrhythmias and those used to extend the refractory period in the presence of persistent electromagnetic interference. One refractory period that is commonly used in atrial-triggered bradycardia pacing modes (e.g., DDD or VDD) is the post-ventricular atrial refractory period, or PVARP, which is an atrial sensing refractory period that begins with a sensed or paced ventricular event. One purpose of the PVARP is to prevent pacemaker-mediated tachycardia by preventing the atrial sensing channel from sensing an atrial depolarization retrogradely conducted to the atria from the ventricles. This can be done by setting the duration of the PVARP to be longer than the retrograde ventriculo-atrial conduction time. The duration of the PVARP also limits the upper rate response of an atrial-triggered pacing mode to intrinsic atrial beats. In order to preserve these functions, the PVARP may be left unaffected when the cross-chamber atrial sensing blanking interval is shortened or eliminated in accordance with the invention.

In most cardiac rhythm management devices, the signals from the sense amplifier of a sensing channel are applied to one input of a comparator circuit whose other input is connected to a reference potential. Only when an electrogram signal from the sense amplifier exceeds the reference potential will it be treated as a detected cardiac depolarization event such as an R-wave or a P-wave. The reference potential may thus be referred to as a sensing threshold. Some devices implement the comparator function in software such that a digitized electrogram signal value is compared with a reference value in order to detect the depolarization event. In a further refinement of the present invention, when the cross-chamber blanking interval for the atrial sensing channel is either shortened or eliminated, the specificity of the channel is increased in order to lessen the possibility of detecting a far-field ventricular depolarization.

Figure 3A:
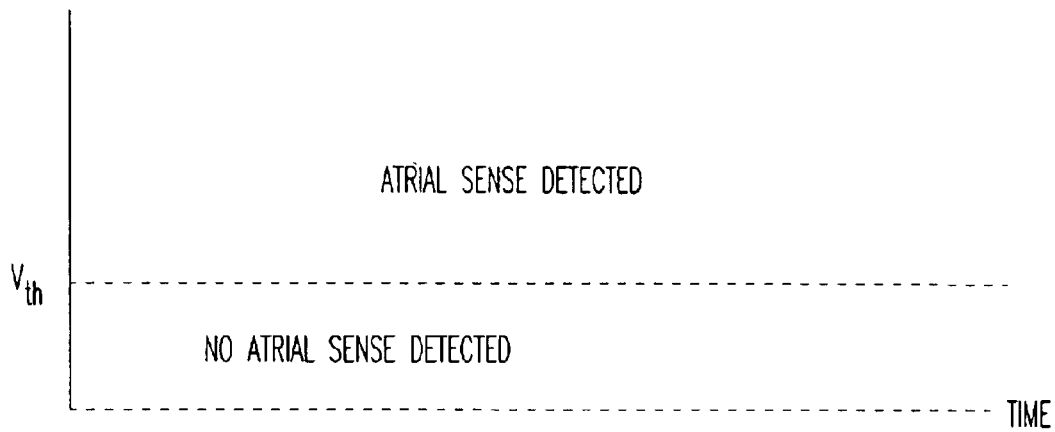
FIGS. 3A–B illustrate atrial sensing thresholds.
Figure 3B:
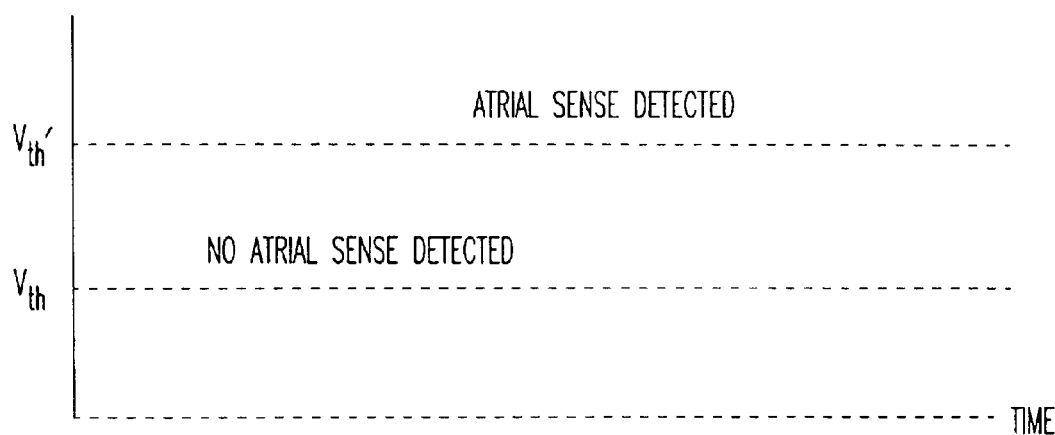

One way to increase the specificity of a sensing channel is to raise the sensing threshold. FIG. 3A shows the sensing threshold $V_{th}$ for the atrial sensing channel during normal operating conditions. A sensing signal in the atrial sensing channel that exceeds $V_{th}$ is thus interpreted as an atrial sense. FIG. 3B shows a modified atrial sensing threshold $V_{th}'$ which is higher than the previous threshold $V_{th}$. This sensing threshold is applied when the atrial cross-chamber blanking interval is shortened. Although the probability of a sensing a far-field ventricular depolarization is increased when the cross-chamber blanking interval is shortened, the increase is lessened by requiring a larger amplitude far-field signal before a sense is detected. In one embodiment, when the cross-chamber blanking interval is shortened, the atrial sensing threshold is raised to a specified value. In another embodiment, the atrial sensing threshold is made to vary in accordance with the detected ventricular rate in tandem with variable shortening of the cross-chamber blanking interval.

Another way to increase the specificity of the atrial sensing channel is to filter the sense signal with a narrower bandwidth filter than is used under normal operating conditions. Such a filter may be designed with a passband that more nearly matches the frequency content of an atrial depolarization waveform.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device comprising:
    means for sensing atrial depolarizations;
    means for sensing ventricular depolarizations;
    means for detecting an atrial sense when a signal generated by the atrial sensing means exceeds an atrial sensing threshold value;
    means for detecting a ventricular sense when a signal generated by the ventricular sensing means exceeds a ventricular sensing threshold value;
    means for measuring atrial and ventricular rates;
    means for blanking the atrial sensing means for a blanking interval after detection of a ventricular sense; and,
    means for shortening the blanking interval when a ventricular rate above a specified limit rate is detected.

2. The device of claim 1 further comprising means for leaving unaffected a post-ventricular atrial refractory period used to limit an atrial-triggered pacing rate and prevent pacemaker mediated tachycardia when the blanking interval is shortened.

3. The device of claim 1 further comprising means for increasing the specificity of the atrial sensing means when the blanking interval is shortened.

4. The device of claim 1 further comprising means for raising the atrial sensing threshold value when the blanking interval is shortened.

5. The device of claim 1 further comprising means for filtering sensed signals from the atrial sensing means with a narrower bandwidth when the blanking interval is shortened.

6. The device of claim 1 further comprising means for discontinuing blanking of the atrial sensing means when a ventricular rate above a specified limit value is detected.

7. The device of claim 1 further comprising means for delivering defibrillation shocks to an atrium.

8. The device of claim 1 further comprising means for delivering atrial pacing pulses in accordance with an anti-tachycardia pacing mode when an atrial rate in a tachycardia detection zone is detected.

9. The device of claim 1 further comprising means for delivering an atrial tachyarrhythmia therapy if an atrial tachyarrythmia is detected wherein the atrial tachyarrhythmia therapy is selected between atrial anti-tachycardia pacing and an atrial defibrillation shock.

10. The device of claim 1 further comprising means for delivering ventricular pacing pulses in accordance with an anti-tachycardia pacing mode when a ventricular rate in a tachycardia detection zone is detected.

11. The device of claim 1 further comprising means for delivering a ventricular defibrillation shock when a ventricular rate in a fibrillation detection zone is detected.

12. The device of claim 1 further comprising means for varying the specificity of the atrial sensing channel in accordance with the detected ventricular rate.

13. The device of claim 1 further comprising means for varying the length of the atrial sensing blanking interval in accordance with the detected ventricular rate.

14. A method for operating a cardiac rhythm management device comprising:
    sensing atrial depolarizations through an atrial sensing channel;

sensing ventricular depolarizations through a ventricular sensing channel;

interpreting sensed signals generated by the sensing channels and detecting atrial or ventricular senses when the sensed signals exceed respective atrial and ventricular sensing threshold values;

measuring atrial and ventricular rates;

blanking the atrial sensing channel after detection of a ventricular sense for a specified blanking interval; and, shortening the blanking interval for the atrial sensing channel when a ventricular rate above a specified limit rate is detected;

delivering ventricular pacing pulses in accordance with an anti-tachycardia pacing mode when a ventricular rate in a tachycardia detection zone is detected;

delivering a ventricular defibrillation shock when a ventricular rate in a fibrillation detection zone is detected; and, delivering an atrial tachyarrhythmia therapy if an atrial rate in an atrial tachyarrythmia zone is detected.

15. The method of claim 14 wherein the atrial tachyarrhythmia therapy is selected from atrial anti-tachycardia pacing and an atrial defibrillation shock.

16. A method for operating a cardiac rhythm management device comprising:

sensing atrial depolarizations through an atrial sensing channel;

sensing ventricular depolarizations through a ventricular sensing channel;

interpreting sensed signals generated by the sensing channels and detecting atrial or ventricular senses when the sensed signals exceed respective atrial and ventricular sensing threshold values;

measuring atrial and ventricular rates;

blanking the atrial sensing channel after detection of a ventricular sense for a specified blanking interval;

shortening the blanking interval for the atrial sensing channel when a ventricular rate above a specified limit rate is detected; and, varying the specificity of the atrial sensing channel in accordance with the detected ventricular rate.

17. The method of claim 16 further comprising varying the length of the atrial sensing blanking interval in accordance with the detected ventricular rate.

* * * * *